United States Patent
Niess et al.

[11] 3,956,326
[45] May 11, 1976

[54] 3-AMINO-ISOTHIAZOLO[3,4-D]PYRIMIDINES

[75] Inventors: Rolf Niess, Schifferstadt; Heinz Eilingsfeld, Frankenthal, both of Germany

[73] Assignee: BASF Aktiengesellschaft, Ludwigshafen (Rhine), Germany

[22] Filed: Oct. 21, 1974

[21] Appl. No.: 516,613

[30] Foreign Application Priority Data
Nov. 2, 1973  Germany............................ 2354685

[52] U.S. Cl. .................. 260/256.5 R; 260/247.1 L
[51] Int. Cl.[2]............... C07D 239/00; C07D 295/00
[58] Field of Search ............................ 260/256.5 R

[56] References Cited
OTHER PUBLICATIONS
Chemical Abstracts, 70:3918m, (1969).

*Primary Examiner*—Leonard Schenkman
*Attorney, Agent, or Firm*—Johnston, Keil, Thompson & Shurtleff

[57] ABSTRACT

3-aminoisothiazolo[3,4-d]pyrimidines of the formula:

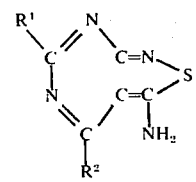

wherein
$R^1$ is a substituent; and
$R^2$ is hydrogen or methyl. The compounds are valuable diazo components for the production of azo dyes.

4 Claims, No Drawings

3-AMINO-ISOTHIAZOLO[3,4-D]PYRIMIDINES

The invention relates to compounds of the formula (I):

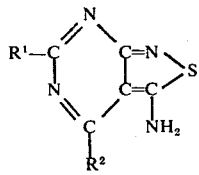
(I)

in which
R¹ is hydrogen, unsubstituted or substituted alkyl, cycloalkyl, aralkyl or aryl, disubstituted amino or substituted mercapto; and
R² is hydrogen or methyl, and also to a process for the production of these compounds.

Unsubstituted and substituted alkyl includes particularly alkyl of one to eight carbon atoms which may bear for example hydroxy, alkoxy, alkylsulfonyl or phenylsulfonyl as substituents.

Specific examples are methyl, ethyl, propyl, butyl, pentyl, hexyl, octyl, β-hydroxyethyl, β-methoxyethyl, β-ethoxyethyl, β-butoxyethyl, β-hydroxypropyl, β-methoxypropyl, β-ethoxypropyl, β-butoxypropyl, methysulfonylmethyl, ethylsulfonylmethyl, phenylsulfonylmethyl and methylphenylsulfonylmethyl.

Unsubstituted and substituted cycloalkyl groups include for example cyclohexyl and methylcyclohexyl.

Aralkyl and aryl radicals are particularly phenylalkyl and phenyl groups which may bear alkyl, alkoxy or halogen, such as methyl, ethyl, methoxy, ethoxy, chloro or bromo as substituents in the phenyl ring.

Specific examples are benzyl, phenylethyl, phenylpropyl, phenylbutyl, their derivatives bearing methyl, methoxy, ethoxy, chloro or bromo as substituents, and the corresponding substituted phenyl radicals.

Disubstituted amino radicals include particularly dialkylamino groups of one to four carbon atoms in the alkyl and which may bear hydroxy, alkoxy of one to four carbon atoms, alkanoyloxy of two to six carbon atoms or carbalkoxy of a total of two to five carbon atoms as substituents.

Radicals R also include pyrrolidino, piperidino, morpholino, thiomorpholino-S-dioxide and N-methylpiperazino.

Examples of disubstituted amino radicals R (in addition to those already specified) are:

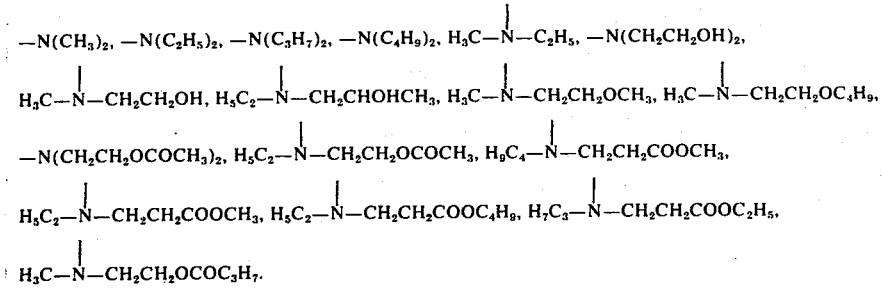

Examples of substituted mercapto radicals are: alkylmercapto of one to eight carbon atoms which may bear carbalkoxy of a total of two to five carbon atoms or optionally N-substituted carbamoyl of a total of two to twelve carbon atoms as substituents and also arylmercapto, benzylmercapto, acetonylmercapto and benzoylmethylmercapto. Examples of specific radicals are: -SCH₃, -SC₂H₅, -SC₃H₇, -SC₄H₉, -SC₅H₁₁, -SC₆H₁₃, -SC₇H₁₅, -SC₈H₁₇, -SCH₂COOR³, -SCH₂CH₂COOR³ (where R³ is alkyl of one to four carbon atoms), also

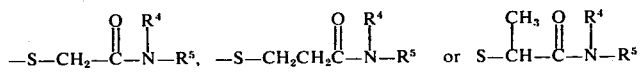

(where R⁴ and R⁵ may be hydrogen or alkyl of one to four carbon atoms or R⁴ or R⁵ may be cyclohexyl, benzyl, phenylethyl or phenyl and R⁴ and R⁵ together with the nitrogen may be the radical of morpholine, piperidine or pyrrolidine, and also C₆H₅S, ClC₆H₄S, H₃CC₆H₄S, (H₃C)₂C₆H₃S, H₃COC₆H₄S or H₅C₂OC₆H₄S.

Compounds of formula (Ia):

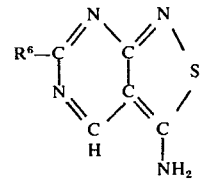
(Ia)

in which R⁶ is hydrogen, phenyl, phenyl bearing methyl or ethyl as substituents, disubstituted amino or substituted mercapto are particularly valuable, especially because of their easy accessibility.

Preferred mercapto radicals include alkylmercapto of one to six carbon atoms. Preferred amino radicals include dialkylamino of a total of two to eight carbon atoms and also pyrrolidino, piperidino, morpholino and N-methylpiperazino.

For the production of the 3-aminoisothiazolo[3,4-d]pyrimidines a 4-aminopyrimidino-5-carboxylic thioamide of formula (II):

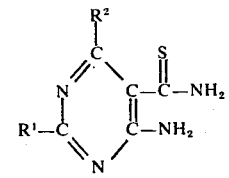
(II)

in which R¹ and R² have the above meanings may be subjected to oxidative cyclization. The 4-aminopyrimidino-5-carboxylic thioamides of formula (II) may be obtained by a conventional method (see for example "The Chemistry of Heterocyclic Compounds", Interscience Publishers 1962, "The Pyrimidines", D. J. Brown; or Houben-Weyl, "Methoden der organischen Chemie", volume 9) by adding on H₂S to an appropriate nitrile. The nitriles may also be prepared by known methods (see for example "Advances in Organic Chemistry", volume 7, "The Chemistry of Cyclic Enaminonitriles and o-Aminonitriles", Editor: E. C. Taylor, Interscience Publishers, 1970).

Oxidative cyclization of 4-aminopyrimidino-5-carboxylic thioamides is conveniently carried out in the presence of an inert solvent and/or suspension agent at a temperature of from 0° to 120°C and preferably at from 15° to 80°C.

Examples of oxidizing agents for effecting the cyclization are hydrogen peroxide and derivatives of hydrogen peroxide such as Caro's acid, persulfuric acid, peracetic acid, perphthalic acid or perbenzoic acid and also bromine, chlorine, iodine or chromic acid.

Examples of solvents and/or suspension agents are: water, lower fatty acids, alkanols, ethers, halohydrocarbons, lower fatty acid esters, amides and mineral acids. The process may also be carried out in the presence of a base, for example pyridine, sodium hydroxide, or potassium hydroxide. Specific convenient reaction media include: methanol, ethanol, n-propanol, isopropanol, butanol, methyl glycol, dimethyl glycol, acetic acid, propionic acid, chloroform, dimethylformamide, dimethyl sulfoxide, water and sulfuric acid.

Preferred oxidizing agents are hydrogen peroxide and bromine. Preferred solvents include methanol, ethanol, methyl glycol, dimethylformamide and dimethyl sulfoxide.

To carry out the process the 4-aminopyrimidino-5-carboxylic thioamide is conveniently dissolved or suspended in the solvent used and the oxidizing agent is added. It is advantageous to stir the reaction mixture and to cool it if necessary or to heat it for a short time after the initial exothermic reaction has subsided. As a rule from 1 to 6 and preferably from 1 to 3 equivalents of oxidizing agent is used per mole of thioamide. A larger excess of oxidizing agent may be used however provided the substituents are inert to the oxidizing agent under the reaction conditions chosen.

The reaction is generally ended after a short time.

Working up does not offer any difficulty and depends on the oxidizing agent and solvent used. When an alkanol and hydrogen peroxide are used the 3-aminoisothiazolo[3,4d]pyrimidine usually crystallizes out during the reaction or may be precipitated by adding water to the reaction mixture. The solids may be isolated for example by filtration or centrifuging.

When an acid has been used as the solvent or when an oxidizing agent has been used which forms an acid under the reaction conditions the corresponding salt of the aminoisothiazole may be obtained. To isolate the free amine the reaction mixture may be added to icewater and the whole made neutral to weakly alkaline by adding for example caustic soda solution, caustic potash solution, aqueous ammonia, sodium carbonate or potassium carbonate so that the compound of formula (I) is precipitated.

The new 3-aminoisothiazole[3,4-d]pyrimidines are valuable diazo components for the production of dyes.

The following Examples illustrate the invention. The parts given in the Examples are parts by weight. They bear the same relation to parts by volume as the kilogram to the liter.

EXAMPLE 1

A solution of 19.2 parts of bromine in 40 parts of chloroform is allowed to drip within five minutes into a solution of 12 parts of 2-methylmercapto-4-aminopyrimidino-5-carboxylic thioamide in 120 parts of chloroform while stirring at room temperature. A weakly exothermic reaction takes place; the temperature rises to 32°C. After the whole has been stirred for another hour it is suction filtered, and the residue is made into a paste with 250 parts of water and then made weakly alkaline with 20% aqueous caustic soda solution. The solid is suction filtered, washed with water and dried in vacuo at 80°C.

The yield is 11 parts (91.7% of theory). The melting point is 228° to 231°C.

A sample which has been recrystallized from toluene has a melting point of 230° to 231°C.

Analysis: $C_6H_6N_4S_2$ (198.14)
calculated: C 36.37  H 3.05  N 28.28  S 32.30
found:      C 36.1   H 3.3   N 27.8   S 32.1.

EXAMPLE 2

The procedure described in Example 1 is repeated but ethyl acetate is used instead of chloroform. The yield is 66% theory.

EXAMPLE 3

9.6 parts of bromine is allowed to drip slowly into a solution of 6 parts of 2-methylmercapto-4-aminopyrimidino-5-carboxylic thioamide in 15 parts of dimethylformamide while stirring at 20° to 25°C. A yellow solid forms. After the whole has been stirred for another hour 150 parts of water is added and a weakly alkaline reaction is set up by adding concentrated ammonia solution. The solid is suction filtered, washed with water and dried at 80°C in vacuo. The yield is quantitative and the melting point is 225° to 230°C.

EXAMPLE 4

20 parts of 40% peracetic acid is allowed to drip into a suspension of 6 parts of 2-methylmercapto-4-aminopyrimidine-5-carboxylic thioamide in 50 parts of glacial acetic acid, the temperature rising to 70°C. After thirty minutes 200 parts of water is added, and the residue is suction filtered, washed with water and dried. The yield is 33% of theory.

EXAMPLE 5

6.6 parts of 30% hydrogen peroxide is allowed to drip during 5 minutes into a solution of 6 parts of 2-methylmercapto-4-aminopyrimidine-5-carboxylic thioamide in 50 parts of dimethylformamide. The temperature rises to 30°C and a yellow solid is precipitated. After stirring for an hour, 100 parts of water is added, and the residue is suction filtered, washed with water and dried at 80°C in vacuo. The yield is 80% of theory.

EXAMPLE 6

20 parts of 50% hydrogen peroxide is dripped in the course of thirty minutes into a suspension of 20 parts of 2-methylmercapto-4-aminopyrimidino-5-carboxylic acid thioamide in 150 parts of methanol while stirring. The temperature is kept below 50°C by external cooling. After the whole has been stirred for another hour the product is suction filtered, washed with a small amount of methanol and dried in vacuo at 100°C. The yield is 90% of theory.

In the following Table:
Ex = Example No.;
Y% = yield in %;

m.p. °C = melting point in °C after recrystallization from methyl glycol (MG); ethanol (ET); dimethylformamide (DMF); water (W);
EF:MW = empirical formula/molecular weight;

C%:H%:N%:O%:S%: = percentage of carbon:hydrogen:nitrogen:oxygen:sulfur found by analysis (upper line calculated; lower line as found);

i-p = isopropyl.

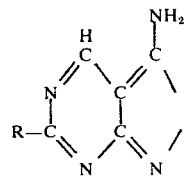

| Ex | R | Y% | m.p. °C | EF:MW | C% | H% | N% | O% | S% |
|---|---|---|---|---|---|---|---|---|---|
| 7 | SCH$_2$CH$_3$ | 69.2 | MG 174–176 | C$_7$H$_8$N$_4$S$_2$ 212 | 39.63 39.9 | 3.77 4.0 | 26.40 26.0 | | 30.20 29.9 |
| 8 | S(CH$_2$)$_2$CH$_3$ | 87.5 | ET 166–167 | C$_8$H$_{10}$N$_4$S$_2$ 226.19 | 42.48 42.8 | 4.46 4.4 | 24.77 24.8 | | 28.9 28.0 |
| 9 | S(CH$_2$)$_3$CH$_3$ | 88.8 | ET 172–174 | C$_9$H$_{12}$N$_4$S$_2$ 240.22 | 45.00 44.8 | 5.04 5.3 | 23.23 23.1 | | 26.64 26.5 |
| 10 | S(CH$_2$)$_5$CH$_3$ | 62.1 | ET 166–168 | C$_{11}$H$_{16}$N$_4$S$_2$ 268.27 | 49.25 49.3 | 6.01 6.0 | 20.89 20.8 | | 23.86 23.6 |
| 11 | S(CH$_2$)$_6$CH$_3$ | 89.5 | DMF/W 160–162 | C$_{12}$H$_{18}$N$_4$S$_2$ 282.3 | 51.05 51.0 | 6.43 6.3 | 19.85 20.0 | | 22.67 22.9 |
| 12 | SCH$_2$C$_6$H$_5$ | 95.0 | DMF/W 181–182 | C$_{12}$H$_{10}$N$_4$S$_2$ 274.23 | 52.55 52.2 | 3.68 3.7 | 20.43 20.7 | | 23.34 23.0 |
| 13 | SCH$_2$COC$_6$H$_5$ | 80.3 | ET 118–120 | C$_{13}$H$_{10}$N$_4$OS$_2$ 302.24 | 51.66 51.5 | 3.34 3.4 | 18.54 18.8 | 5.29 5.1 | 21.17 21.3 |
| 14 | SCH$_2$COOC$_2$H$_5$ | 70.2 | ET 166–168 | C$_9$H$_{10}$N$_4$O$_2$S$_2$ 270.2 | 40.00 39.8 | 3.73 3.5 | 20.74 20.9 | 11.84 11.5 | 23.68 24.0 |
| 15 | SCH$_2$CONH$_2$ | 100 | DMF/W 201–202 | C$_7$H$_7$N$_5$OS$_2$ 241.17 | | | | | 26.52 26.3 |
| 16 | SCH$_2$CONH—C$_6$H$_5$ | 84.3 | DMF/W 178–180 | C$_{13}$H$_{17}$N$_5$SO$_2$ 323.31 | | | | | 19.72 19.5 |
| 17 | SCH$_2$CONHCH$_2$C$_6$H$_5$ | 83.7 | DMF/W 168–169 | C$_{14}$H$_{13}$N$_5$OS$_2$ 331.28 | | | | | 19.32 19.0 |
| 18 | SCH$_2$CON(C$_2$H$_5$)$_2$ | 87.1 | DMF/W 181–182 | C$_{11}$H$_{15}$N$_5$OS$_2$ 297.27 | | | | | 21.52 21.6 |
| 19 | SCH$_2$CON—(i-p)$_2$ | 91.2 | DMF/W 166–168 | C$_{15}$H$_{23}$N$_5$OS$_2$ 353.37 | | | | | 18.12 18.5 |
| 20 | SCH$_2$CON(piperidinyl) | 85.4 | DMF/W 183–185 | C$_{12}$H$_{15}$N$_5$OS$_2$ 309.28 | | | | | 20.69 20.5 |
| 21 | S(CH$_2$)$_2$CON(C$_2$H$_5$)$_2$ | 85.1 | DMF/W 181–183 | C$_{12}$H$_{17}$N$_5$OS$_2$ 311.28 | 46.30 | 5.50 | 22.50 | 5.14 | 20.56 20.3 |
| 22 | S(CH$_2$)$_2$CON(piperidinyl) | 75.3 | DMF/W 189–190 | C$_{13}$H$_{17}$N$_5$OS$_2$ 323.31 | 48.29 | 5.30 | 21.66 | 4.95 | 19.80 19.9 |
| 23 | N(CH$_3$)CH$_3$ | 96.1 | MG 235–236 | C$_7$H$_9$N$_5$S 195.18 | 43.01 43.3 | 4.63 4.8 | 35.95 35.3 | | 16.41 16.1 |
| 24 | morpholinyl | 89.5 | DMF/W 219–221 | C$_9$H$_{11}$N$_5$OS 237.22 | 45.6 45.7 | 4.64 4.6 | 29.51 29.6 | 6.75 7.0 | 13.5 13.4 |
| 25 | piperidinyl | 88.3 | DMF/W 208–209 | C$_{10}$H$_{13}$N$_5$S 235.24 | 51.1 51.1 | 5.53 5.7 | 29.77 29.9 | | 13.6 13.5 |
| 26 | pyrrolidinyl | 90.1 | DMF/W 229–231 | C$_9$H$_{11}$N$_5$S 221.22 | 48.86 48.6 | 5.01 5.1 | 31.66 31.3 | | 14.47 14.4 |
| 27 | H | 68.2 | ET >300 | C$_5$H$_4$N$_4$S 152.11 | 39.48 39.8 | 2.65 2.4 | 36.84 36.9 | | |
| 28 | CH$_2$C$_6$H$_5$ | 86.4 | DMF/W 170–173 | C$_{12}$H$_{10}$N$_4$S 242.23 | 59.5 59.7 | 4.16 4.4 | 23.15 23.4 | | 13.23 11.9 |
| 29 | C$_6$H$_5$ | 96.5 | MG/W 208–210 | C$_{11}$H$_8$N$_4$S 228.21 | 57.89 57.5 | 3.53 3.4 | 24.6 25.0 | | 14.02 13.8 |
| 30 | C$_6$H$_4$CH$_3$(p) | 90.1 | ET 227–229 | C$_{12}$H$_{10}$N$_4$S 242.23 | 59.5 59.8 | 4.16 4.3 | 23.13 22.8 | | 13.21 12.8 |
| 31 | C$_6$H$_4$OCH$_3$(p) | 95.4 | DMF 216–219 | C$_{12}$H$_{10}$N$_4$OS 258.23 | 55.80 55.6 | 3.88 4.2 | 21.70 21.6 | 6.2 6.6 | 12.41 12.1 |
| 32 | C$_6$H$_4$Cl(p) | 91.2 | DMF 234–235 | C$_{11}$H$_7$N$_4$SCl 262.5 | 50.03 49.9 | 2.66 2.8 | 21.35 21.7 | | 12.43 12.1 |
| 33 | CH$_2$SO$_2$C$_6$H$_5$ | 90.4 | ET 175 | C$_{12}$H$_{10}$N$_4$O$_2$S$_2$ 306.23 | 47.06 46.7 | 3.29 3.5 | 18.30 17.9 | | |

EXAMPLE 34

3 parts of 50% hydrogen peroxide is allowed to drip at a temperature of from 45° to 50°C into a suspension of 6.45 parts of 4-amino-2,6-dimethylpyrimidino-5-carboxylic thioamide in 50 parts of methanol and the whole is stirred for another hour. The solid is suction filtered at room temperature, washed with a small amount of methanol and dried at 80°C.

The yield is quantitative; the melting point is 192° to 193°C.

After a sample has been recrystallized from ethanol it has a melting point of 211° to 212°C.

Analysis for $C_{13}H_{12}N_4S$ (256.26) calculated: C 60.93 H 4.72 N 21.87 S 12.49 found: C 61.2 H 4.9 N 21.5 S 12.2.

We claim:

1. A compound of the formula

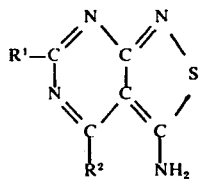

wherein $R^1$ is hydrogen; alkyl of 1 to 8 carbon atoms; alkyl of 2 to 8 carbon atoms substituted by hydroxy or alkoxy of 1 to 4 carbon atoms; methylsulfonyl-, ethylsulfonyl-, phenylsulfonyl- or methylphenylsulfonylalkyl of 1 to 4 carbon atoms in the alkyl; cyclohexyl; methylcyclohexyl; phenylalkyl of 1 to 4 carbon atoms in the alkyl; phenylalkyl substituted by chloro, bromo, methyl, ethyl, methoxy or ethoxy and having 1 to 4 carbon atoms in the alkyl; phenyl; phenyl substituted by chloro, bromo, methyl, ethyl, methoxy or ethoxy; dialkylamino of 1 to 4 carbon atoms in the alkyl; dialkylamino of 1 to 4 carbon atoms in the alkyl and substituted by hydroxy; alkylmercapto of 1 to 8 carbon atoms; alkylmercapto of 1 to 4 carbon atoms substituted by alkoxycarbonyl of 1 to 4 carbon atoms in the alkoxy, carbamoyl, N-$C_1$ to $C_4$-alkylcarbamoyl, N,N-$C_1$ to $C_4$-dialkylcarbamoyl, N-cyclohexylcarbamoyl, N-benzylcarbamoyl, N-phenylethylcarbamoyl or N-phenylcarbamoyl; benzylmercapto; phenylmercapto; phenylmercapto substituted by chloro, methyl, methoxy or ethoxy; $CH_3COCH_2S$ or $C_6H_5COCH_2S$ and $R^2$ is hydrogen or methyl.

2. A compound as claimed in claim 1 of the formula

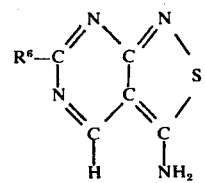

wherein $R^6$ is hydrogen, phenyl, phenyl substituted by methyl or ethyl, alkylmercapto of 1 to 8 carbon atoms or alkylmercapto of 1 to 4 carbon atoms substituted by $C_1$ to $C_4$-alkoxycarbonyl.

3. A compound according to the formula in claim 1, wherein $R^1$ is alkylmercapto of 1 to 6 carbon atoms.

4. the compounds as claimed in claim 1 of the formula

\* \* \* \* \*

UNITED STATES PATENT AND TRADEMARK OFFICE
CERTIFICATE OF CORRECTION

PATENT NO. : 3,956,326
DATED : May 11, 1976
INVENTOR(S) : NIESS et al

It is certified that error appears in the above-identified patent and that said Letters Patent are hereby corrected as shown below:

In the Abstract, delete

"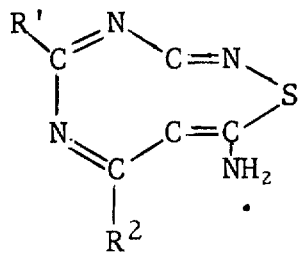"

and substitute

--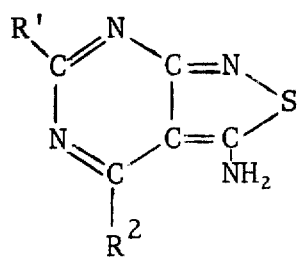--

Signed and Sealed this

Eighth Day of March 1977

[SEAL]

Attest:

RUTH C. MASON
Attesting Officer

C. MARSHALL DANN
Commissioner of Patents and Trademarks